US008827884B2

(12) United States Patent
Ribbing et al.

(10) Patent No.: US 8,827,884 B2
(45) Date of Patent: Sep. 9, 2014

(54) ONCOLOGY THERAPIES EMPLOYING RADIOACTIVE SEEDS

(75) Inventors: Carolina Ribbing, Aachen (DE); Michael Overdick, Emmendingen (DE)

(73) Assignee: Koninklijke Philips N.V., Eindhoven (NL)

( * ) Notice: Subject to any disclaimer, the term of this patent is extended or adjusted under 35 U.S.C. 154(b) by 14 days.

(21) Appl. No.: 13/386,911

(22) PCT Filed: Jul. 6, 2010

(86) PCT No.: PCT/IB2010/053094
§ 371 (c)(1),
(2), (4) Date: Jan. 25, 2012

(87) PCT Pub. No.: WO2011/015958
PCT Pub. Date: Feb. 10, 2011

(65) Prior Publication Data
US 2012/0123189 A1    May 17, 2012

Related U.S. Application Data

(60) Provisional application No. 61/231,705, filed on Aug. 6, 2009.

(51) Int. Cl.
*A61N 5/00* (2006.01)
*A61M 36/00* (2006.01)
*A61K 51/12* (2006.01)

(52) U.S. Cl.
CPC .................................. *A61K 51/1255* (2013.01)
USPC ............................................................ 600/8

(58) Field of Classification Search
CPC .............. A61K 51/12; A61K 51/1241; A61K 51/1255; A61K 51/1262; A61K 51/1265; A61N 2005/1024
USPC ............................................. 600/8; 424/1.29
See application file for complete search history.

(56) References Cited

U.S. PATENT DOCUMENTS 4,510,924 A * 4/1985 Gray ........................... 424/1.61
4,612,009 A   9/1986 Drobnik et al.
(Continued)

FOREIGN PATENT DOCUMENTS

DE    3521893 A1    12/1985
EP    0668088 A1    8/1995
(Continued)

OTHER PUBLICATIONS http://web.archive.org/web/20081217021126/http://en.wikipedia.org/wiki/Half-life.*
"Half-life," Wikipedia, as captured on Dec. 17, 2008 from http://web.archive.org/web/20081217021126/http://en.wikipedia.org/wiki/Half-life, retrieved on Aug. 30, 2013.*

(Continued)

*Primary Examiner* — Samuel Gilbert
*Assistant Examiner* — Thaddeus Cox

(57) ABSTRACT

An oncology therapy method comprises implanting a radioactive seed (10, 20, 30, 40, 50) in an oncology subject (S). In some embodiments the radioactive seed comprises a radioactive material (12, 32, 33, 42) including at least one radioisotope disposed in a biodegradable host (14, 24, 25, 44) configured to biodegrade over a therapy time period when implanted in the oncology subject. In some embodiments the radioactive seed is implanted in soft tissue of an oncology subject (S), and the radioactive seed comprises a radioactive material (12, 32, 33, 42) including at least one radioisotope disposed in a host material (14, 24, 25, 44) having softness comparable with or softer than the soft tissue into which the radioactive seed is implanted.

12 Claims, 3 Drawing Sheets

(56) References Cited

U.S. PATENT DOCUMENTS

Figure 1:
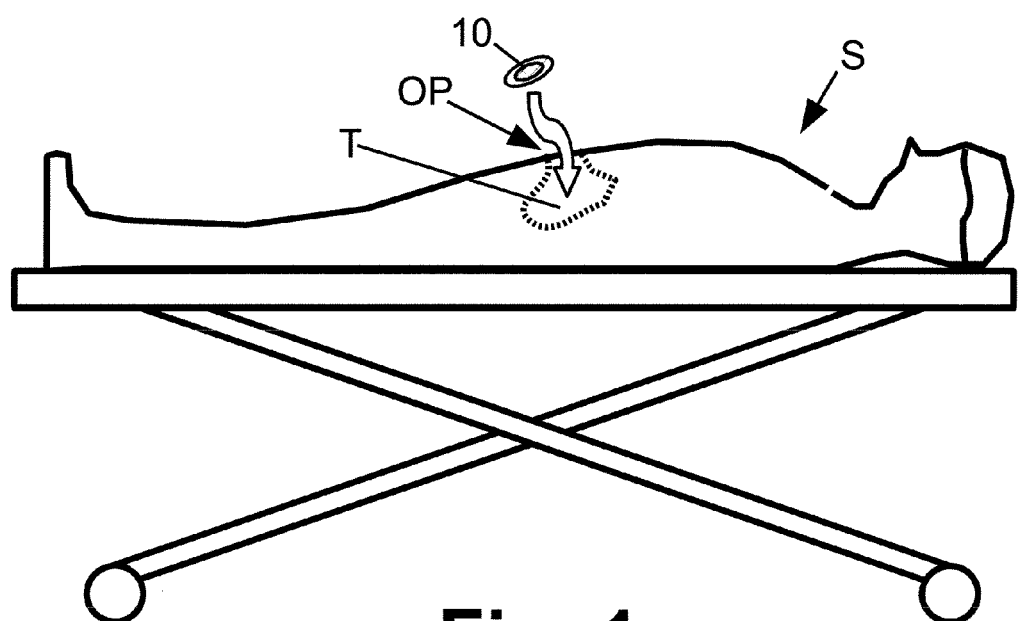

| | | | |
|---|---|---|---|
| 5,336,505 | A | 8/1994 | Ng et al. |
| 5,397,572 | A | 3/1995 | Coombes et al. |
| 5,449,679 | A | 9/1995 | Leonard |
| 6,248,057 | B1 | 6/2001 | Mavity et al. |
| 6,309,380 | B1 | 10/2001 | Larson et al. |
| 6,575,888 | B2 | 6/2003 | Zamora et al. |
| 6,746,661 | B2 | 6/2004 | Kaplan |
| 7,358,223 | B2 | 4/2008 | Zhao et al. |
| 7,959,900 | B2 * | 6/2011 | Peng et al. ............... 424/1.11 |
| 2001/0044567 | A1 * | 11/2001 | Zamora et al. ............... 600/3 |
| 2003/0104031 | A1 | 6/2003 | Dumont et al. |
| 2003/0120355 | A1 | 6/2003 | Hafeli et al. |
| 2006/0083729 | A1 | 4/2006 | Kusanagi et al. |
| 2006/0188543 | A1 | 8/2006 | Feng |
| 2007/0078480 | A1 | 4/2007 | Belenkaya et al. |
| 2008/0004483 | A1 | 1/2008 | Tarone et al. |
| 2008/0249398 | A1 * | 10/2008 | Harder et al. ............... 600/424 |
| 2009/0131735 | A1 * | 5/2009 | Drobnik et al. ............... 600/8 |
| 2010/0056843 | A1 * | 3/2010 | Fisher et al. ............... 600/8 |

FOREIGN PATENT DOCUMENTS

| | | | |
|---|---|---|---|
| FR | 2836921 | A1 | 9/2003 |
| WO | 9827962 | A2 | 7/1998 |
| WO | 9827963 | A2 | 7/1998 |
| WO | 9855101 | A1 | 12/1998 |
| WO | 0044682 | A1 | 8/2000 |
| WO | 0064538 | A1 | 11/2000 |
| WO | 0130409 | A1 | 5/2001 |
| WO | 0154764 | A2 | 8/2001 |
| WO | 0226215 | A2 | 4/2002 |
| WO | 02068000 | A2 | 9/2002 |
| WO | 03039655 | A2 | 5/2003 |
| WO | 2004041318 | A1 | 5/2004 |
| WO | 2005007802 | A2 | 1/2005 |
| WO | 2005087274 | A1 | 9/2005 |
| WO | 2006065951 | A2 | 6/2006 |

OTHER PUBLICATIONS

Assmann, W., et al.; Biodegradable radioactive implants for glaucoma filtering surgery produced by ion implantation; 2007; Nuclear Instruments and Methods in Physics Research; B 257; pp. 108-113.

Azab, A. K., et al.; Crosslinked chitosan implants as potential degradable devices for brachytherapy: In vitro and in vivo analysis; 2006; Journal of Controlled Release; 111(3)281-289.

Azab, A. K., et al.; Prevention of tumor recurrence and distant metastasis formation in a breast cancer mouse model by biodegradable implant of 131I-norcholesterol; 2007; Journal of Controlled Release; 123(2)116-122.

Baglan, K. L., et al.; The use of high-dose-rate brachytherapy alone after lumpectomy in patients with early-stage breast cancer treated with breast-conserving therapy; 2001; I. J. Radiation Oncology Biology Physics; 50(4)1003-1011.

Cacaina, D., et al.; The behavior of selected yttrium containing bioactive glass microspheres in simulated body environments; 2008; J. Mater Sci: Mater Med; 19(3)1225-1233.

Conzone, S. D., et al.; Biodegradable radiation delivery system utilizing glass microspheres and ethylenediaminetetraacetate chelation therapy; 2004; J. Biomedical Materials Research; 70A(2)256-264.

Goh, A. S-W., et al.; A novel approach to brachytherapy in hepatocellular carcinoma using a phosphorous 32 (32P) brachytherapy delivery device-a first-in-man study; 2007; Int. J. Radiation Oncology Biol. Phys.; 67(3)786-792.

Hafeli, U. O., et al.; Magnetically directed poly(lactic acid) 90Y-microspheres: Novel agents for targeted intracavitary radiotherapy; 1994; J. of Biomedical Materials Research; 28(8)901-908.

Hafeli, U. O., et al.; Polymeric Radiopharmaceutical Delivery Systems; 1992; Radioactivity & Radiochemistry; 3(4) 11-14.

Liu, W., et al.; Injectable intratumoral depot of thermally responsive polypeptide-radionuclide conjugates delays tumor progression in a mouse model; 2010; Journal of Controlled Release; 144:2-9.

Mumper, R. J., et al.; Neutron-Activated Holmium-166-Poly (L-Lactic Acid) Microspheres: A Potential Agent for the Internal Radiation Therapy of Hepatic Tumors; 1991; J. of Nuclear Medicine; 32(11)2139-2143.

* cited by examiner

ONCOLOGY THERAPIES EMPLOYING RADIOACTIVE SEEDS

CROSS REFERENCE TO RELATED APPLICATIONS

This application claims the benefit of U.S. provisional application Ser. No. 61/231,705 filed Aug. 6, 2009, which is incorporated herein by reference.

DESCRIPTION

The following relates to the medical arts, oncology arts, oncological therapy arts, and related arts.

A known oncology therapy is the implantation of radioactive seeds proximate to a cancerous tumor or region. The radioactive seeds for oncological therapy applications typically consist of a metallic shell of titanium or another metal which encases a designed amount of the therapeutic gamma emitting radioisotope. In some therapy protocols the seeds are permanently implanted in order to deliver continuous therapeutic radiation to the site of the cancer; whereas, in other therapy protocols seeds are implanted temporarily (sometime for as short a time as a few minutes) and then removed in order to deliver a controlled radiation dose targeted to the site of the cancer.

Such existing techniques have some drawbacks. The radioactive seeds are mechanically different from the surrounding tissue, and the seeds can move around over time. Seed movement results in poor or non-existent dose control. The radioactive seeds also deliver a radiation profile over time that is controlled by the radioactivity decay profile of the seed. This profile typically has an exponential decay shape, leading to high initial radiation output when first implanted, which can result in undesirably high radiation exposure to the patient, to medical personnel performing the seed implantation procedure, and to other persons in the vicinity. Indeed, in some therapy protocols the patient is asked to avoid prolonged close human contact (for example, at a distance of less than one meter) due to concern about "second-hand" radiation exposure.

The seeds may also not comport effectively with the shape and size of the region to be irradiated. This can be addressed to some extent by implanting a distribution of seeds, but the individual seeds still act as point radiation sources, and additionally have a tendency to move around within the patient. Still further, seeds which are metallic in composition present obstacles to certain medical procedures such as magnetic resonance (MR) imaging.

The following provides new and improved apparatuses and methods which overcome the above-referenced problems and others.

In accordance with one disclosed aspect, a radioactive seed for use in oncology therapy comprises: a radioactive material including at least one radioisotope; and a biodegradable host in which the radioactive material is disposed, the biodegradable host configured to biodegrade over a therapy time period when implanted in an oncology subject.

In accordance with another disclosed aspect, a radioactive seed for use in oncology therapy comprises: a radioactive material including at least one radioisotope; and a host material in which the radioactive material is disposed, the host material having softness comparable with or softer than soft tissue of an oncology subject into which the radioactive seed is to be implanted.

In accordance with another disclosed aspect, an oncology therapy method comprises implanting a radioactive seed as set forth in one of the two immediately preceding paragraphs in an oncology subject.

In accordance with another disclosed aspect, an oncology therapy method comprises implanting a radioactive seed in an oncology subject, the radioactive seed comprising a radioactive material including at least one radioisotope disposed in a biodegradable host configured to biodegrade over a therapy time period when implanted in the oncology subject.

One advantage resides in providing enhanced control over the radiation output over time during an oncology therapy session.

Another advantage resides in providing enhanced control over the positioning of radioactive seeds in an oncology therapy session.

Further advantages will be apparent to those of ordinary skill in the art upon reading and understanding the following detailed description.

FIG. 1 diagrammatically illustrates an oncology therapy session including implantation of one or more radioactive seeds.

Figure 2:
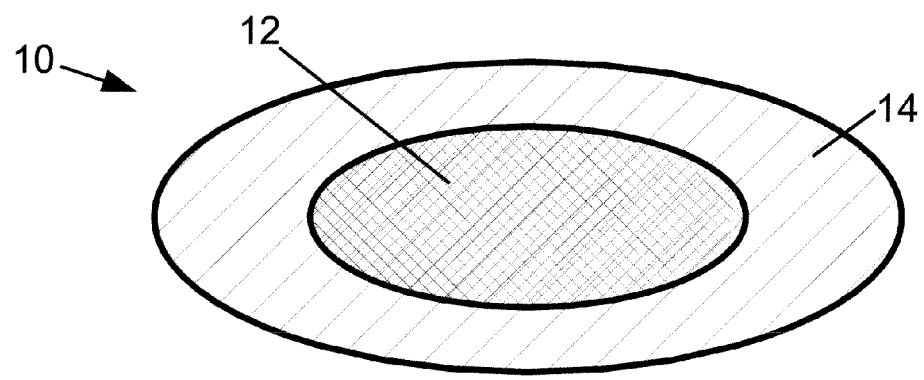
Figure 4:
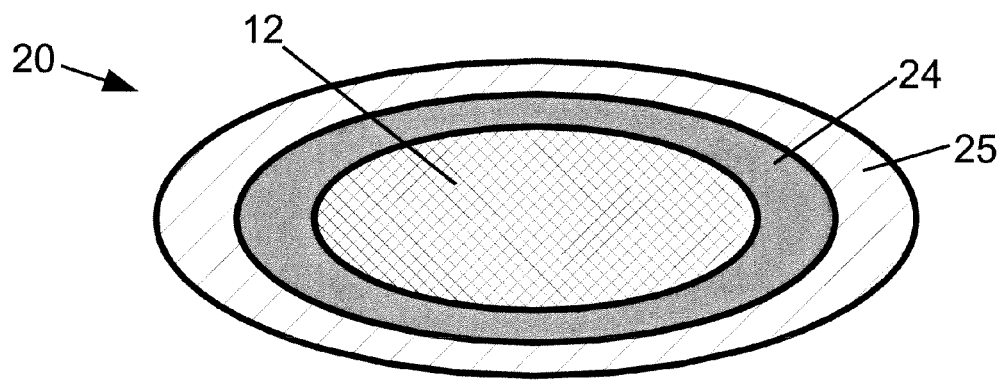
Figure 5:
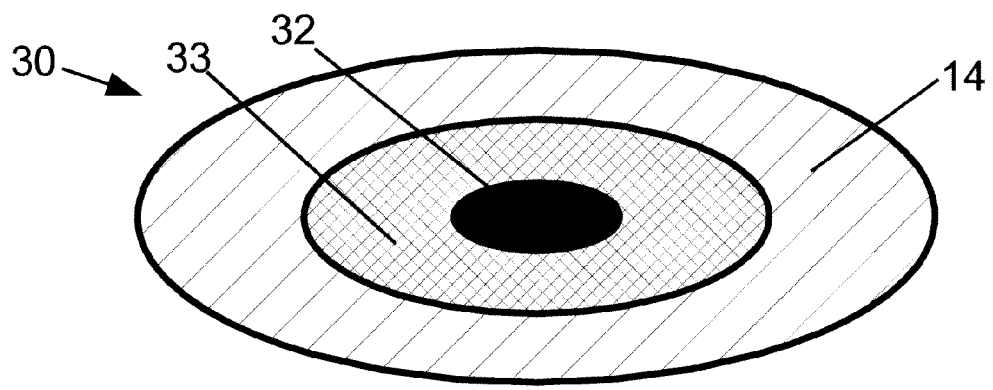

FIGS. 2, 4, and 5 diagrammatically illustrate cross-sectional views of three illustrative radioactive seeds having the form of ellipsoidal capsules.

Figure 3:
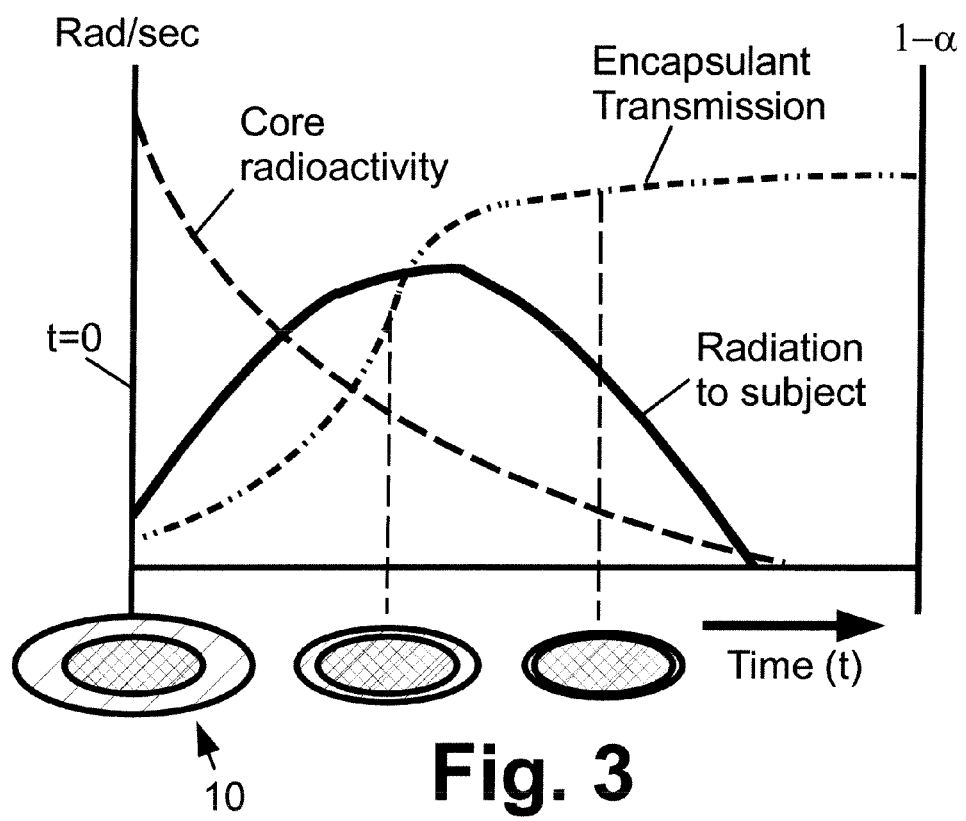

FIG. 3 diagrammatically plots radiation output to the oncology subject over time using the radioactive seed of FIG. 2, with the biodegradation of the biodegradable encapsulant diagrammatically shown below the abscissa.

Figure 6:
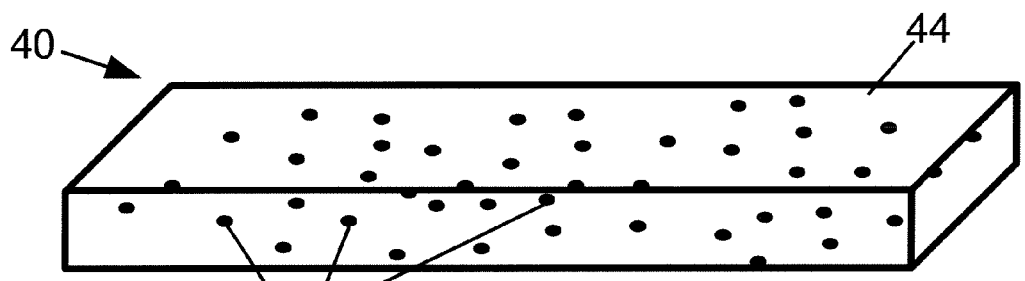
Figure 7:
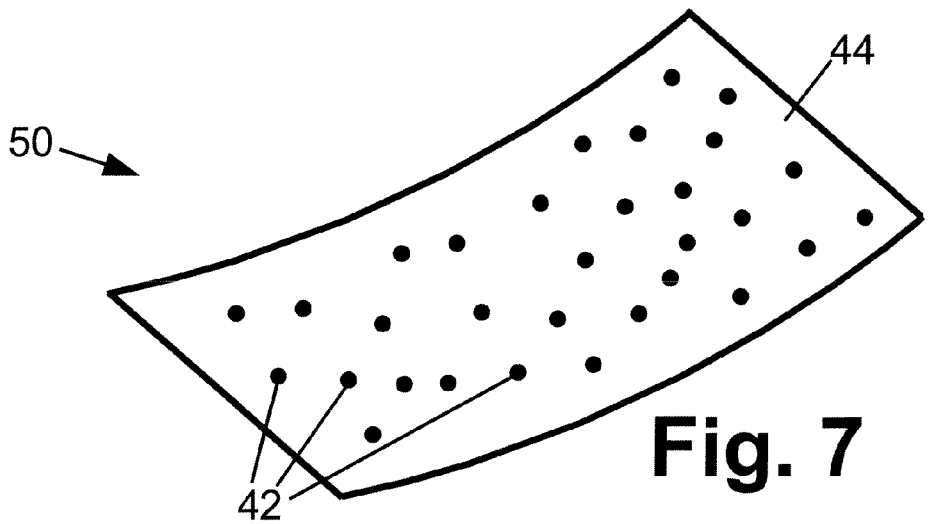

FIGS. 6 and 7 diagrammatically illustrate perspective views of two illustrative radioactive seeds in which radioactive material is distributed in a host matrix material.

With reference to FIG. 1, an oncology subject S is illustrated undergoing an oncology therapy session employing one or more radioactive seeds 10. The illustrated oncology subject S is a human subject; however, a veterinary subject such as a dog, cat, or so forth is also contemplated. In the procedure, a surgeon or other qualified medical professions makes an incision or other insertion opening OP enabling the radioactive seed 10 to be implanted at a target location T that is proximate to a tumor, tumor cavity, lesion, or other (cancerous) malignancy. The illustrated insertion opening OP is diagrammatic—in general, the opening can be a conventional surgical opening, an arthroscopic opening, an opening formed "automatically" as the subject's skin is pierced by a needle or other interventional instrument, or so forth. The insertion opening OP is generally located close to the target location T where the radioactive seed 10 is to be implanted, as diagrammatically shown in FIG. 1, although in the case of arthroscopic surgery or other interventional procedures employing an interventional instrument the opening may be located some distance away from the target location where the radioactive seed is to be implanted.

The radioactive seed 10 is passed through the insertion opening OP and disposed at the target location T proximate to the tumor, lesion, or other cancerous malignancy. Although only one radioactive seed 10 is illustrated in FIG. 1, the number of radioactive seeds implanted in an oncology therapy session may be one, two, three, four, five, ten, or more. The number of implanted seeds is selected based on the size or area of the target location and the amount of radiation to be delivered, compared with the size and radiation output of the one or more radioactive seeds 10. In most oncological applications, the target location T comprises soft tissue such as fat, muscle, or an internal organ such as the liver, prostate, breast, ovary, bladder, rectum, pancreas, lung, esophagus, brain, or so forth. However, it is also contemplated for the target location to comprise hard tissue such as bone or cartilage.

With continuing reference to FIG. 1 and with further reference to FIG. 2, the radioactive seed 10 has the form of an ellipsoidal capsule, and includes a radioactive core 12 surrounded by an encapsulant 14 that serves as a biodegradable host configured to biodegrade over a therapy time period when implanted in the oncology subject S. The radioactive core 12 includes one or more radioisotopes that emit therapeutic radiation that is the active component of the oncology therapy. For example, the radioisotope in the radioactive core 12 may emit gamma particles, beta particles, or so forth. The radioactive seed 10 has an ellipsoid shape; however, other shapes including spherical capsules are also contemplated.

With continuing reference to FIGS. 1 and 2 and with further reference to FIG. 3, in some embodiments the biodegradable material of the encapsulant 14 is selected to have substantial absorption for the radiation emitted by the radioactive core 12. FIG. 3 illustrates a benefit of this in producing a controlled radiation emission over time during the course of the oncology therapy. As shown in FIG. 3, the radioisotope of the radioactive core 12 has radioactivity that decreases exponentially over time. As is known in the art, such a radioactivity-versus-time profile can be characterized by a half-life indicating the time period over which the radiation output of the radioactive core 12 decreases to one-half of its initial radiation output. Thus, in the absence of the encapsulant 14 the oncology subject S would experience a high radiation level initially that would rapidly decrease over time. Since the radiation output of the radioactive core 12 is highest at the time of implantation, this also means that the surgeon or other person performing the oncology therapy is exposed to a high radiation level (which is typically countered by the use of radiation-shielding gloves or other protective apparel).

With continuing reference to FIGS. 1-3, the radiation-absorbing biodegradable encapsulant 14 absorbs a substantial fraction of the radiation output by the radioactive core 12. The absorption is suitably quantified by an absorption or attenuation coefficient $\alpha$; conversely, the transmission through the encapsulant 14 can be characterized by $1/\alpha$. The radiation output delivered to the oncology subject S at any given time is therefore the radiation output of the radioactive core 12 (which decreases over time by an amount characterized by the half-life) scaled by the transmission of the biodegradable encapsulant 14 (which increases over time as the biodegradable encapsulant 14 degrades after implantation in the subject S).

The radiation output over time can be represented by $R(t)=R_o \cdot \exp(-t/\tau)$ where $R_o$ is the initial radiation output of the radioactive core 12 at the time of implantation (that is, at time t=0) and $\tau$ is a time constant related to the half life of the radioisotope. The transmission of the biodegradable encapsulant 14 can be represented as $T(t) \propto \exp(-\alpha \cdot d(t))$ where $\alpha$ is the absorption or attenuation coefficient (transmission is suitably quantified as $1-\alpha$) and $d(t)$ is the (average or other aggregate) thickness of the encapsulant at time t. The encapsulant thickness $d(t)$ decreases over time due to biodegradation of the encapsulant, and so the transmission $T(t)$ is expected to increase over time. The total radiation output to the subject is $R_{out}(t)=R(t)T(t)$, which includes the core emission term $R(t)$ which decreases with time and the encapsulant transmission term $T(t)$ which increases with time.

As diagrammatically shown in FIG. 3, the radiation output $R_{out}(t)$ can therefore be configured to have a peak at a designed time after implantation (where in FIG. 3 the time t=0 is the time of implantation of the seed 10). The time of peak radiation is controlled by the half life of the radioisotope (related to the time constant $\tau$) of the radioactive core 12, the initial thickness of the encapsulant 14, and the rate at which the encapsulant thickness $d(t)$ decreases over time due to biodegradation. Advantageously, the radiation output of the seed at time t=0 is lower than the peak radiation output, which enhances safety of the surgeon or other qualified person performing the oncology therapy.

With reference to FIG. 4, an alternative radioactive seed 20 has the same radioactive core 12 as the seed 10 of FIG. 1, but has the encapsulant 14 replaced by a double-layered encapsulant including inner and outer concentric encapsulant layers 24, 25. The use of a multiple-layered encapsulant 24, 25 (where the number of encapsulant layers may be the illustrated two layers, or three layers, or four layers, or so forth) provides additional degrees of freedom for tailoring the encapsulant absorption and the rate of encapsulant degradation so as to more precisely tailor the radiation output to the oncology subject over time. For example, the two encapsulant layers 24, 25 may have similar biodegradability, but the inner encapsulant layer 24 may have a higher absorption coefficient $\alpha$ (and hence lower transmission for a given thickness) as compared with the outer encapsulant layer 25.

In some embodiments, the outer encapsulant layer or layers may be biodegradable while the innermost encapsulant layer is not biodegradable. This advantageously ensures that the radioactive core is not directly exposed to the patient as the biodegradable layer or layers dissolve.

With reference to FIG. 5, a radioactive seed 30 provides a different approach for providing further control parameters. The seed 30 has the same single-layer encapsulant 14 as the seed 10, but employs a different radioactive core which includes a central core 32 and a concentrically surrounding outer core 33. For example, the central core 32 may include a gamma-emitting radioisotope while the outer core 33 may include a beta-emitting radioisotope. By using two (or more) different radioisotopes with different half lives, the shape of the radioactive core radiation output function $R(t)$ can be tailored.

Although FIG. 5 illustrates an arrangement in which the two radioisotopes are segregated into different spatial regions 32, 33 of the radioactive core, in other embodiments the two (or more) different radioisotopes can be intermixed in the same space. For example, it is contemplated for the radioactive core 12 of the seed 10 of FIG. 2 to have two (or more) different radioisotopes substantially uniformly distributed through the core 12.

The radioactive seeds 10, 20, 30 of FIGS. 2, 4, and 5 are formed as capsules comprising a radioactive core surrounded by a biodegradable host formed as an encapsulant around the core. In other embodiments, the biodegradable host comprises a biodegradable matrix material and the radioactive material is distributed in the biodegradable matrix material.

With reference to FIG. 6, for example, a radioactive seed 40 includes radioactive material 42 distributed in a biodegradable matrix material 44 that forms the radioactive seed as a slab. FIG. 6 diagrammatically illustrates the distribution of the radioactive material 42 in the biodegradable matrix material 44 as discrete "points" in the diagrammatic drawing. The radioactive material 42 may in general be distributed in the biodegradable matrix material 44 in various ways, such as: (i) as a plurality of rigid elements distributed in the biodegradable matrix material; (ii) as a substance dissolved in the biodegradable matrix material (where the term "dissolved" is to be broadly understood to encompass variations such as a radioactive material covalently bound to the matrix material as in the case of FDG in which the $^{18}$F radioactive material is bound to deoyxglucose); (iii) as particles dispersed in the biodegradable matrix material; or so forth. In some embodiments, the radioactive material 42 including one or more radioisotopes are dissolved or dispersed in the matrix material 44 by being covalently or ionically bound to the molecules of the matrix material 44. In some embodiments, the radioactive material 42 including one or more radioisotopes are distributed as particles dispersed in the biodegradable matrix material by being trapped in pores of the matrix material 44, or contained in micelles, capsules, nanoshells or (low-Z) microparticles which are distributed in the matrix material 44.

Because the radioactive material 42 is distributed substantially uniformly in the biodegradable matrix material 44, it follows that the amount of radiation delivered to the oncology subject S depends on the size (i.e., volume or weight) of the radioactive seed 40, possibly with some secondary dependence on the geometry of the radioactive seed 40. As a result, it is contemplated for the seed 40 to be cut from a larger block of material, and the oncology treatment protocol can be expressed in terms of the amount (e.g., volume or weight) of the seed material that is implanted. Alternatively, the radioactive material 42 can be added to the biodegradable matrix material 44 in different concentrations.

With reference to FIG. 7, a radioactive seed 50 comprises the same radioactive material 42 distributed in the same biodegradable matrix material 44 as in the seed 40 of FIG. 6, but in the case the radioactive seed 50 the material is formed as a pliable sheet of biodegradable matrix material.

In another contemplated geometry (not illustrated), the host material 44 is formed as a medical suture thread containing radioactive material 42. One contemplated application for such a geometry is prostate cancer brachytherapy, for which seed displacement is known to be problematic. In such an embodiment, the host material 44 with the suture geometry can be either biodegradable over time, or alternatively is not biodegradable.

In such embodiments, it is to be appreciated that the term "radioactive seed" is used herein to denote the combination of the radioactive material 42 and the host material 44. In similar fashion, in the embodiments of FIGS. 2, 4, and 5 the term "radioactive seed" denotes the combination of the radioactive core 12, 32, 33 and the encapsulant 14, 24, 25.

In general, the host material 14, 24, 25, 44 can be rigid or pliable. For embodiments such as those of FIGS. 6 and 7, in which the host material 44 is a biodegradable matrix material, using a pliable material advantageously enables the radioactive seed 40, 50 to be a pliable radioactive seed that can be bent or shaped to facilitate implantation of the pliable radioactive seed in the oncology subject S.

In general, the host material 14, 24, 25, 44 can be hard or soft. For implantation in which the target location T comprises soft tissue such as fat, muscle, or an internal organ such as the liver, prostate, breast, ovary, bladder, rectum, pancreas, lung, esophagus, brain, or so forth, it is advantageous for the host material 14, 24, 25, 44 to have a softness comparable with or softer than the soft tissue. This reduces the likelihood of disengagement of the implanted radioactive seed, discomfort to the subject, and so forth. On the other hand, if the target location T comprises hard tissue such as bone or cartilage, then it is advantageous for the host material 14, 24, 25, 44 to have a hardness comparable with the hardness of the hard tissue.

Moreover, it is contemplated to employ a pliable and/or soft host material that is not biodegradable. Embodiments in which the host material is pliable but not biodegradable provide the benefit of enabling bending or shaping the radioactive seed to facilitate the implantation. Embodiments in which the host material is soft (e.g., having softness comparable with or softer than soft tissue of the implantation target location T) but not biodegradable provide the benefit of reduced likelihood of disengagement of the implanted radioactive seed, reduced discomfort to the subject, and so forth.

Another contemplated alternative embodiment is to have the radioactive material 42 embedded in a central portion of the host material 44, where the host material 44 is selected such that the radioactive material 42 diffuses to spread over a larger volume of the host material 44 over time at a known rate so as to achieve a controlled radiation output to the patient over time similar to that shown in FIG. 3. The rate of spread can be tailored by control of host material properties such as cross-linking, density, or so forth.

Having provided some illustrative embodiments with reference to FIGS. 1-7, some further aspects are set forth.

The host material 14, 24, 25, 44 is optionally selected to provide imaging contrast for an imaging modality such as magnetic resonance (MR) imaging, transmission computed tomography (CT) imaging, or so forth. For example, the host material may optionally include a low concentration of a paramagnetic material (for example, a biocompatible gadolinium-based material) dispersed in the host material to enhance its contrast in MR imaging, so that MR imaging can be used to monitor the position of the seed and, in the case of a biodegradable host material, to monitor the dissolution of the host material over time. This in turn enables dose monitoring via the imaging.

The disclosed radioactive seeds 10, 20, 30, 40, 50 can be used substantially similarly to existing radioactive seeds that omit the host material 14, 24, 25, 44. For example, in prostate cancer treatment, a temporary implant can employ a high-dose rate (HDR) source of Ir-192 as the radioisotope. For permanent implants, isotopes with lower energies and shorter half-lives are suitably used, such as Pd-103 or I-125 radioisotopes. For capsule embodiments, the radioactive core 12 can comprise a sealed titanium container containing gamma emitting radioactive isotopes, and the seeds including the encapsulant 14, 24, 25 are suitably implanted at the target location T using one or more needles which are inserted at (or pierce the subject's skin to define) the insertion opening OP under ultrasound guidance.

For prostate cancer treatment with low dose rate (LDR) Pd-103, a typical protocol involves administration of 125-145 Gy from 60-120 seeds inserted via 20-30 needles. The seeds are typically a few millimeters long and a millimeter or so in diameter, and have 67 MBq/seed on implantation. The implantation takes about 1-2 hrs and is guided by transrectal ultrasound and flouroscopy under narcosis or spinal anaesthesia. The target location T in this case is the whole prostate, with 2-4 mm marginal, should get 100% of the prescribed dosis, whereas the urethra should receive max 150% and the rectum wall max 100% of the prescribed dosis. Because of the short range of Pd gamma radiation, only 10% of the prescribed dose results 1.5 cm outside the prostate. After implantation, a cytoscopy is preferably performed to verify that no seeds ended up in bladder or in urethra. The patient receives a temporary catheter and can leave the hospital on the same or the following day. The seeds radiate during approximately three months with 5 Gy/24 hrs. Patients are advised to avoid prolonged human contact with less than 1 m distance.

In some suitable embodiments, the host material 14, 24, 25, 44 is a biodegradable gel of a type commercially available for use in cosmetic injections. Some suitable gels include Restylane and Macrolane, which are hyaluronic acid derivates available from Q-Med AB (Uppsala, Sweden). Other suitable host materials include materials used in biodegradable medical sutures, such as polyester, polypropylen, and polydioxanon available from Ethicon GmbH or Johnson & Johnson Medical GmbH.

For embodiments such as those of FIGS. 6 and 7, in which the host material 44 is a biodegradable matrix material, the radioactive material 42 is substantially uniformly distributed in the matrix material 44 which may be a volume filling gel, gelling fluid, foam, slab, sheath, or so forth. A slab such as the seed 40 of FIG. 6 can be inserted into a tumour cavity, for example after surgical breast tumor removal. Similarly, a sheath or sheet such as the seed 50 of FIG. 7 can be placed to line a tumor cavity. A gel, gelling fluid or foam can be injected directly into a tumourous tissue. Reducing the number of punctions of tumourous tissue can be advantageous for not spreading malignant cancer cells in the body of the patient. Increased control of the placement of radioactive sources also allows for better dose control and minimizes radiation of healthy tissue in comparison to normal LDR sources. In general, the host matrix material 44 can be formed into any shape conducive to implantation, such as: slabs, sheaths, microparticles, beads, capsules, strings, deformable gel, foam or gelling fluid. Some suitable materials for the host matrix material 44 include various polymers such as polyethylene glycol (PEG), dextrane, sol-gel glass, silicone, orthoester polymers, starch gels, hyaluoronic acid derivates such as Restylane, polyethylenimine, poliglecapron, polyglactin, polypropylen, polyamid, polyester, polyglycolic acid, poly-(p-) dioxanone or polydioxine, lactide copolymer, polymers of 1,3-trimethylene carbonate, and so forth. There are merely illustrative examples, and other host materials are also contemplated.

Another advantage of the embodiments of FIGS. 6 and 7 is compatibility with beta emitting radioisotopes. Conventional radioactive seeds employing titanium encasement are not compatible with beta emitting radioisotopes because the titanium blocks the beta particles. In contrast, the radioactive material 42 distributed in the matrix material 44 can readily include a beta emitting radioisotope.

In embodiments in which the host matrix material 44 is biodegradable, it is generally advantageous for the radioisotope of the radioactive material 42 to have a half life that is substantially shorter than a time period for the biodegradable host material 44 to biodegrade when implanted in the oncology subject S. This ensures that the host matrix material 44 holds the radioactive material 42 in place at the target location T for the duration of the oncology therapy, after which biodegradation of the host matrix material 44 releases the material 42 (which at this point is substantially nonradioactive) to be removed by usual elimination pathways.

In general, the radioactive material 12, 32, 33, 42 can include any oncologically therapeutic radioisotope, such as $^{43}$K which decays via $\beta^-$ (310 keV) with $T_{1/2}$=22 h into $^{43}$Ca which is stable. The native Ca will form low-toxicity molecules/compounds in the human body. If the decay time of the host material 14, 24, 25, 44 is about nine days (which is roughly ten times the half-life of $^{43}$K), then a distribution of the radioactive material in the body upon biodissolution of the host material 14, 24, 25, 44 is minimal, ensuring minimal irradiation of non-target tissue. Some suitable alternative beta ($\beta$) emitters include e.g. $^{48}$Sc decaying into $^{48}$Ti (E=225 keV, $T_{1/2}$=44 h), $^{32}$P decaying into $^{32}$S (E=690 keV, $T_{1/2}$=14 d), $^{33}$P decaying into $^{33}$S (E=76 keV, $T_{1/2}$=25 d), $^{35}$S decaying into $^{35}$Cl (E=49 keV, $T_{1/2}$=88 d), $^{48}$V decaying into $^{48}$Ti (E=230 keV, $T_{1/2}$=16 d), $^{42}$K decaying into $^{42}$Ca (E=1550 keV, $T_{1/2}$=12 h), $^{45}$Ca decaying into $^{45}$Sc (E=77 keV, $T_{1/2}$=160 d), $^{90}$Y decaying into $^{90}$Zr (E=934 keV, $T_{1/2}$=64 h). Suitable gamma/x-ray emitters include e.g. $^{103}$Pd decaying into $^{103}$Rh (E=21 keV, $T_{1/2}$=19 d), $^{125}$I decaying into $^{125}$Te (E=28 keV, $T_{1/2}$=60 d), and $^{51}$Cr decaying into $^{51}$V (E=320 keV, $T_{1/2}$=28 d). These are merely illustrative examples, and other radioisotopes and combinations of radioisotopes are also contemplated.

As further illustrative examples, a slab of matrix material 44 (as in the seed 40 of FIG. 6) may have the distributed radioactive material 42 include an even distribution of a gamma-emitting isotope and an inner coating absorbing low-energy gamma particles and an outer coating containing a beta-emitting isotope. In another example, the matrix material 44 comprises an injectable foam or gel that forms a three-dimensional network before or after injection or has large particle sizes preventing migration from the injection site (that is, the target location T). The viscosity and the range of migration may be tailored by grade of cross-linking, selection of particle size, or so forth. The implant can be formed in situ by gelling, setting, solidification of an injectable fluid, or so forth, and can optionally fill a tumour cavity after surgical removal or intermingle and displace in a fashion analogous to hualuronic acid derivates in healthy tissue. The matrix material 14, 24, 25, 44 can be tailored to degrade at a controlled rate depending on its composition and physical form to suit the individual application. The matrix allows controlled release of radiation in the subject S.

In addition to the radioactive loading, it is contemplated for the matrix material 44 to further include a distribution or coating of drugs, diagnostic agents or so forth, such as anti-cancer drugs for continuos or delayed local delivery or image enhancing agents. For example, e.g. an x-ray opaque material, a magnetic resonance (MR) contrast agent, or air bubbles may be incorporated in the matrix for x-ray, MR, or ultrasound imaging visibility.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A radioactive seed for use in oncology therapy, the radioactive seed comprising:

a radioactive material including at least one radioisotope; and a biodegradable host in which the radioactive material is disposed, the biodegradable host configured to biodegrade over a therapy time period when implanted in an oncology subject;

wherein the radioactive material defines a radioactive core and the biodegradable host defines a biodegradable encapsulant surrounding the radioactive core;

wherein the biodegradable encapsulant is absorbing for at least one type of radiation emitted by the radioactive material to control the radiation versus time delivered to the oncology subject by radiation absorption that varies with time as the biodegradable encapsulant degrades over the therapy time period when implanted in the oncology subject;

wherein the at least one radioisotope has a half life that is shorter than a time period for the biodegradable host to biodegrade when implanted in the oncology subject, the half life of the at least one radioisotope respective to the time period for the biodegradable host to biodegrade being effective for the biodegradable host to hold the radioactive material in place at a target location in the oncology subject for the therapy time period, after which biodegradation of the biodegradable host releases the radioactive material; and wherein the radioactive seed is configured by the biodegradable encapsulant to have radiation output at a time of implantation that is lower than a peak radiation output that occurs at a time after the time of implantation.

2. The radioactive seed as set forth in claim 1, wherein the biodegradable encapsulant comprises a plurality of concentric biodegradable encapsulant layers at least one of which is partially absorbing for at least one type of radiation emitted by the radioactive material.

3. The radioactive seed as set forth in claim 1, wherein the radioactive material includes a beta emitting radioisotope.

4. A radioactive seed for use in oncology therapy, the radioactive seed comprising:
   a radioactive material including at least one radioisotope; and
   a biodegradable host in which the radioactive material is disposed, the biodegradable host configured to biodegrade over a therapy time period when implanted in an oncology subject;
   wherein the radioactive material defines a radioactive core and the biodegradable host defines a biodegradable encapsulant surrounding the radioactive core;
   wherein the biodegradable encapsulant is absorbing for at least one type of radiation emitted by the radioactive material to control the radiation versus time delivered to the oncology subject by radiation absorption that varies with time as the biodegradable encapsulant degrades over the therapy time period when implanted in the oncology subject;
   wherein the at least one radioisotope has a half life that is substantially shorter than a time period for the biodegradable host to biodegrade when implanted in the oncology subject;
   wherein the radioactive seed is configured to deliver radiation versus time $R_{out}(t)=R(t)T(t)$ to the oncology subject from a time of implantation t=0 of where:
      the radioactive core is configured to output radiation $R(t)=R_o\exp(-t/\tau)$ from the time of implantation t=0 where $R_o$ is an initial output of the at least one type of radiation emitted by the radioactive core at t=0 and $\tau$ is a time constant corresponding to the half-life of the radioactive material; and
      the biodegradable encapsulant is configured to exhibit transmission T(t) proportional to $\exp(-\alpha \cdot d(t))$ from the time of implantation t=0 where $\alpha$ is an attenuation coefficient of the biodegradable host and d(t) is an aggregate thickness of the biodegradable encapsulant with d(t) decreasing over time after the time of implantation t=0 due to biodegradation of the biodegradable encapsulant; and
   wherein the radioactive seed is configured by the biodegradable encapsulant to have radiation output $R_o$ at a time of implantation that is lower than a peak of the radiation output $R_{out}(t)=R(t)T(t)$ that occurs at a time after the time of implantation.

5. A radioactive seed for use in oncology therapy, the radioactive seed comprising:
   a radioactive material including at least one radioisotope; and
   a biodegradable host in which the radioactive material is disposed, the biodegradable host configured to biodegrade over a therapy time period when implanted in an oncology subject;
   wherein the radioactive material defines a radioactive core and is not distributed in the biodegradable host, and the biodegradable host defines a biodegradable encapsulant surrounding the radioactive core;
   wherein the biodegradable encapsulant is absorbing for at least one type of radiation emitted by the radioactive material to control the radiation versus time delivered to the oncology subject by radiation absorption that varies with time as the biodegradable encapsulant degrades over the therapy time period when implanted in the oncology subject; and
   wherein the radioactive seed is configured to deliver initial radiation $R_o$ to the oncology subject at a time of implantation and peak radiation greater than the initial radiation $R_o$ at a peak time later than the time of implantation, wherein the peak time is configured by the half-life of the radioisotope and the initial thickness of the biodegradable encapsulant.

6. The radioactive seed of claim 5 wherein the radioactive material includes a plurality of different oncologically therapeutic radioisotopes having half-lives configured to control a radiation versus time profile of oncologically therapeutic radiation emitted by the radioactive material.

7. The radioactive seed as set forth in claim 6, wherein the plurality of different oncologically therapeutic radioisotopes includes a beta emitting oncologically therapeutic radioisotope.

8. The radioactive seed as set forth in claim 6, wherein the plurality of different oncologically therapeutic radioisotopes includes a gamma-emitting oncologically therapeutic radioisotope and a beta-emitting oncologically therapeutic radioisotope.

9. The radioactive seed as set forth in claim 6, wherein the radioactive material defines a radioactive core and the host material defines an encapsulant surrounding the radioactive core.

10. The radioactive seed as set forth in claim 9, wherein the radioactive core includes:
    a central core including a first oncologically therapeutic radioisotope of the plurality of different oncologically therapeutic radioisotopes; and
    an outer core concentrically surrounding the central core and including a second oncologically therapeutic radioisotope of the plurality of different oncologically therapeutic radioisotopes.

11. The radioactive seed as set forth in claim 10, wherein the first oncologically therapeutic radioisotope is a gamma-emitting radioisotope and the second oncologically therapeutic radioisotope is a beta-emitting radioisotope.

12. An oncology therapy method comprising implanting a radioactive seed as set forth claim 5 in an oncology subject, wherein the implanted radioactive seed delivers oncologically therapeutic radiation to the oncology subject in accord with the radiation versus time profile of oncologically therapeutic radiation emitted by the radioactive seed.

* * * * *